United States Patent [19]

Duflos et al.

[11] Patent Number: 5,182,273
[45] Date of Patent: Jan. 26, 1993

[54] SPIROCYCLIC N, O DERIVATIVES OF CYCLOTRIPHOSPHAZENES AND THEIR USE IN THERAPY

[75] Inventors: Alain Duflos; Jean-Francois Patoiseau; Dennis Bigg; Robert Kiss, all of Castres, France

[73] Assignee: Pierre Fabre Medicament, Boulogne, France

[21] Appl. No.: 780,480

[22] Filed: Oct. 22, 1991

[30] Foreign Application Priority Data

Oct. 23, 1990 [FR] France .................................. 90 13103

[51] Int. Cl.$^5$ .................. A61K 31/395; C07D 403/14
[52] U.S. Cl. ...................................... 514/83; 548/957
[58] Field of Search ........................... 548/957; 514/83

[56] References Cited

U.S. PATENT DOCUMENTS 4,595,682  6/1986  Labarre et al. ...................... 514/83

OTHER PUBLICATIONS

S. S. Krishnamurthy et al., J. C. S. Dalton 1980, pp. 840–844.

V. Chandrasekhar et al., Inorg. Nucl. Chem. Letters, 1981, vol. 17, No. 5–6, pp. 181–185.

*Primary Examiner*—Joseph Paul Brust
*Assistant Examiner*—Jacqueline Haley
*Attorney, Agent, or Firm*—Gordon W. Hueschen

[57] ABSTRACT

The present invention relates to compounds of the Formula I:

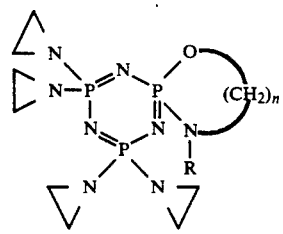

wherein R is hydrogen, alkyl, cycloalkyl, phenyl, or alkylphenyl, and n is 2 through 4, the production thereof, pharmaceutical compositions thereof, and their use in antineoplastic therapy.

15 Claims, No Drawings

SPIROCYCLIC N, O DERIVATIVES OF CYCLOTRIPHOSPHAZENES AND THEIR USE IN THERAPY

FIELD OF THE INVENTION

The present invention relates to new chemical compounds, pharmaceutical compositions thereof, their method of preparation, and their use as antineoplastic medicaments.

The new chemical compounds have the general Formula I

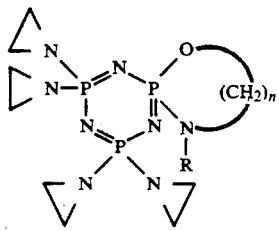

I in which:

R represents hydrogen, a linear, branched, or cyclic $C_{1-6}$ alkyl radical, a phenyl radical, or an alkylphenyl radical phenyl $(CH_2)_m$—, m being 1 to 4 inclusive and, by way of illustration but not of limitation, H, Me, cyclohexyl, phenyl, benzyl, or phenethyl, whereas n=2, 3, or 4.

The present invention also relates to the use of a compound of general Formula I as an antineoplastic medicament and to pharmaceutical compositions containing such active ingredient or principle together with a pharmaceutically-acceptable diluent or carrier.

The pharmaceutical compositions of the present invention embody a compound of general Formula I, possibly together with one or more other active principles, in addition to the same pharmaceutically-acceptable diluent or carrier.

OBJECTS OF THE INVENTION

It is an object of the present invention to provide new chemical compounds, a method for the preparation thereof, pharmaceutical compositions embodying the same, and a method for their use in antineoplastic therapy against neoplastic ailments or conditions susceptible thereto.

Still other objects of the invention will become apparent hereinafter and still further objects of the invention will be apparent to one skilled in the art.

SUMMARY OF THE INVENTION

The invention, then, comprises the following aspects, singly or in combination:

New compounds selected from those having general Formula I as set forth herein; especially such compounds wherein R is selected from hydrogen, methyl, cyclohexyl, benzyl, and phenethyl; especially those compounds set forth herein as Compounds 1 through 9; pharmaceutical compositions of such compounds together with a pharmaceutically-acceptable diluent or carrier; and a method of employing a compound of the invention or a pharmaceutical composition thereof for the antineoplastic treatment or alleviation of a susceptible neoplastic ailment or condition by administration of the same to a patient, whether animal or human, in need thereof.

PREPARATION

The methods of synthesis of the compounds of general Formula I also form a part of the present invention.

Synthesis of the Compounds of General Formula I

The compounds of the present invention are obtained from hexachlorocyclotriphosphazene II via a tetrachlorinated intermediary III, in which the symbols R and n have the same meaning as given for I.

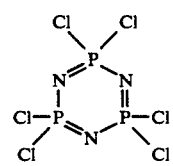

II

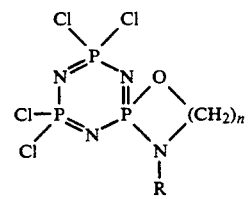

III

Compounds III can be obtained by the method described in the literature, in particular by:

S. S. KRISHNAMURTHY et al., J. C. S. Dalton 1980, pp. 840-844.

V. CHANDRASEKHAR et al., Inorg. Nucl. Chem. Letters, 1981, Vol, 17, No. 5-6, pp. 181-185.

These methods comprise the treatment of hexachlorocyclotriphosphazene ($N_3P_3Cl_6$) with a hydroxyamine IV, preferably in the presence of a hydrochloric acid acceptor such as a tertiary amine, e.g., triethylamine, in a solvent such as tetrahydrofuran (THF).

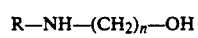

R—NH—$(CH_2)_n$—OH      IV

It is also possible to produce the intermediate III by carrying out the reaction in a two-phase medium such as THF/soda.

The aziridination of the intermediate III, to obtain a compound of the present invention, is effected using aziridine in a solvent such as THF in the presence of a tertiary amine hydrochloric acid acceptor such as, for instance, triethylamine.

The following examples illustrate the invention without limiting its scope.

EXAMPLE 1

Compound 1

4-methyl-7,7,9,9-tetra-1-aziridinyl-7,7,9,9-tetrahydro-1-oxa-4,6,8,10-tetraaza-$5\lambda^5$-7,9-triphosphaspiro-[4,5]-deca-5,7,9-triene

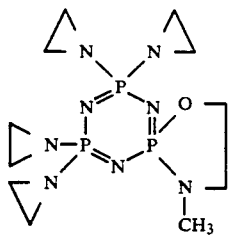

a) Eight (8) g (106 mmols) of N-methyl-2-aminoethanol, 300 ml of THF and 266 ml of 1N aqueous caustic soda are introduced into a one-liter reactor.

With vigorous agitation at 25° C., the $N_3P_3Cl_6$ is introduced all at once, the temperature being maintained below 35° C. After one hour at 30° C., the aqueous phase is saturated with sodium chloride and then, after decantation, extracted with ethyl ether.

The two organic phases, combined, are evaporated to dryness. The residue, taken up in a minimum amount of methylene chloride, is percolated through a silica column (20 g) and eluted with a 1:1 mixture of methylene chloride and ethyl acetate.

After evaporation, the residue is agitated in hexane for 30 minutes.

After filtering and drying at 40° C. under vacuum, 26 g of tetrachlorinated intermediate are obtained.

Yield: 70%—MP=137° C.

b) The compound obtained above (17.5 g, 50 mmols) is placed in solution in 250 ml of THF containing triethylamine (30 g—300 mmols). Aziridine (12.9 g, 300 mmols), diluted in THF (50 ml) is added at −10° C. over the course of 15 minutes.

After agitation for 1 hour at 0° C. and 48 hours at 25° C., the hydrochloride crystals are filtered off and the THF is partially evaporated. The solution obtained is percolated through a silica column (50 g) and eluted with THF (150 ml).

After evaporation to dryness and recrystallization of the residue from THF, the compound 1 (10.5 g) is obtained.

Yield: 56%; MP=170° C.

EXAMPLE 2

Compound 6

11-Phenylmethyl-2,2,4,4-tetra-1-aziridinyl-2,2,4,4-tetrahydro-7-oxa-1,3,5,11-tetraaza-2,4,6$\lambda^5$-triphosphaspiro-[5,5]-undeca-1,3,5-triene.

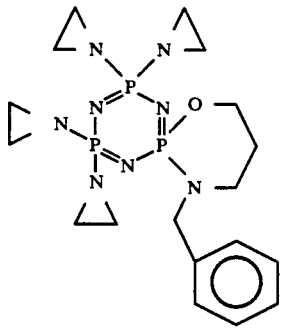

a) Ten (10) g (0.0287 mol) of $N_3P_3Cl_6$ and 165 ml of tetrahydrofuran (THF) are introduced into a double-jacketed 250-ml reactor maintained at 0° C. After dissolution, 8 ml (0.0575 mol) of triethylamine is added and thereafter a solution comprising 5.2 g (0.0316 mol) of 3-benzylaminopropanol in 35 ml of THF is added dropwise over a period of thirty minutes. The reaction mixture is agitated for an additional hour at 0° C. plus an additional fifteen hours at 20° C.

The insoluble material is filtered off and the THF evaporated. The residue is dissolved with a miminum of methylene chloride and the solution thus obtained is percolated through a silica (20 g) column. Upon elution of the column with a mixture of methylene chloride and ethyl acetate 1/1, the fractions containing the product are combined and evaporated and the residue is agitated with a mixture comprising 40 ml of hexane and 5 ml of isopropylether. The crystals are collected by filtration, dried, and rinsed with hexane. After drying at approximately 40° C., one obtains 7 g of 11-phenylmethyl-2,2,4,4-tetrachloro-2,2,4,4-tetrahydro-7-oxa-1,3,5,11-tetraaza-2,4,6$\lambda^5$-triphosphaspiro-[5,5]-undeca-1,3,5-triene.

Yield 55%; MP 112° C.

b) A solution of the compound from the preceding step (5 g, 0.0113 mol) in 65 ml of THF is introduced into a 250-ml double-jacketed reactor. Thereafter 10.9 ml (0.078 mol) of triethylamine is introduced at a temperature of approximately −10° C. A solution comprising 4 ml (0.078 mol) of aziridine and 15 ml of THF is then added dropwise over a period of fifteen minutes. The reaction mixture is agitated at −10° C. for a period of one hour and then at a temperature of 20° C. for a period of 48 hours. The insoluble product is removed by filtration and the THF evaporated to half volume. The remaining solution is chromatographed by passage through a column of silica (50 g) using THF as eluant. Evaporation of the fractions containing the product and recrystallization of the residue from 120 ml of a mixture comprising 50% diisopropyl ether and ethyl acetate affords a crystalline product which is rinsed with diisopropyl ether. After drying at a temperature of about 40° C., 2.65 g of Compound 6 are obtained.

Yield 50%; MP=133° C.

EXAMPLE 3

Compound 9

2,2,4,4-Tetra-1-aziridinyl-2,2,4,4-tetrahydro-7-oxa-1,3,5,12-tetraaza-2,4,6$\lambda^5$-triphosphaspiro-[5,6]-dodeca-1,3,5-triene.

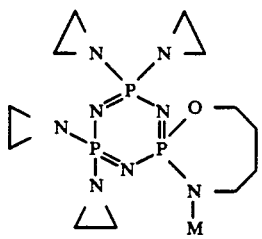

a) Fourteen (14) g (0.04 mol) of $N_3P_3Cl_6$ and 180 ml of THF are introduced into a 250-ml double-jacketed reactor and maintained at 0° C. After dissolution, 9.4 ml (0.067 mol) of triethylamine is added and thereafter a solution comprising 3 g (0.0336 mol) of 4-aminobutanol and 40 ml of THF is added dropwise over a period of fifteen minutes. The reaction mixture is agitated at 0° C. for a period of one hour and then at a temperature of 25°

C. for 24 hours. The insoluble material is filtered off and the THF evaporated. The residue contains mostly the desired product but accompanied by two by-products. Chromatography of the mixture through a column of silica (60 g) and elution of the column with 60% cyclohexane, 20% methylenechloride, and 20% ethylacetate, followed by evaporation of the fractions containing the product, gives a residue which is agitated with hexane. After filtration, rinsing with hexane and drying at a temperature of about 40° C., there is obtained 4.6 g of 2,2,4,4-tetrachloro-2,2,4,4-tetrahydro-7-oxa-1,3,5,12-tetraaza-2,4,6$\lambda^5$-triphosphaspiro-[5,6]-dodeca-1,3,5-triene.

Yield 38%; MP=133° C.

b) The product of the preceding step (4.7 g; 0.0129 mol) is dissolved in 70 ml of THF. The resulting solution is introduced into a 150-ml double-jacketed reactor. Triethylamine (10.8 ml; 0.0775 mol) is added to the solution at a temperature of −10° C. Then, over a period of fifteen minutes, a solution comprising 5.3 ml (0.103 mol) of aziridine and 15 ml of THF is added dropwise. The reaction mixture is stirred at 0° C. over a period of one hour and at 25° C. for 24 hours. The insoluble material is filtered off and the THF evaporated. The residue is then dissolved in a minimum of chloroform and chromatographed by passage through a silica column (45 g) using a mixture of 95% chloroform, 4.5% methanol, and 0.5% ammonia as eluant. The fractions containing the desired product are evaporated and the residue is recrystallized from 30 ml of ethylacetate. After filtration, rinsing with ethylacetate, and drying at a temperature of about 40° C., two (2) g of Compound 9 are obtained.

Yield 40%; MP 129° C.

EXAMPLE 4

Other Compounds of the Invention

Additional examples of related compounds produced in a manner analogous to that given for the production of Compounds 1, 6, and 9 in the foregoing, are as follows:

Compound 2

7,7,9,9-Tetra-1-aziridinyl-7,7,9,9-tetrahydro-1-oxa-4,6,8,10-tetraaza-5$\lambda^5$,7,9-triphosphaspiro-[4,5]-deca-5,7,9-triene.

Compound 3

2,2,4,4-Tetra-1-aziridinyl-2,2,4,4-tetrahydro-7-oxa-1,3,5,11-tetraaza-2,4,6$\lambda^5$-triphosphaspiro-[5,5]-undeca-1,3,5-triene.

Compound 4

11-Cyclohexyl-2,2,4,4-tetra-1-aziridinyl-2,2,4,4-tetrahydro-7-oxa-1,3,5,11-tetraaza-2,4,6$\lambda^5$-triphosphaspiro-[5,5]-undeca-1,3,5-triene.

Compound 5

4-Phenylmethyl-7,7,9,9-tetra-1-aziridinyl-7,7,9,9-tetrahydro-1-oxa-4,6,8,10-tetraaza-5$\lambda^5$,7,9-triphosphaspiro-[4,5]-deca-5,7,9-triene.

Compound 7

4-(2-Phenylethyl)-7,7,9,9-tetra-1-aziridinyl-7,7,9,9-tetrahydro-1-oxa-4,6,8,10-tetraaza-5$\lambda^5$,7,9-triphosphaspiro-[4,5]-deca-5,7,9-triene.

Compound 8

11-(2-Phenylethyl)-2,2,4,4-tetra-1-aziridinyl-2,2,4,4-tetrahydro-7-oxa-1,3,5,11-tetraaza-2,4,6$\lambda^5$-triphosphaspiro-[5,5]-undeca-1,3,5-triene.

The following Table summarizes the characteristics of the nine (9) compounds produced according to the foregoing nine (9) examples.

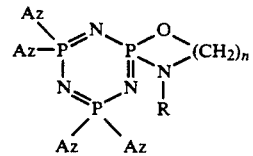

| No. | R | $(CH_2)_n$ | Recryst. Solv. | Yield | Formula | M.W. | MP °C. | RMN $^{31}$P PAs$_2$ | P Spiro | J |
|---|---|---|---|---|---|---|---|---|---|---|
| 1 | CH$_3$ | (CH$_2$)$_2$ | THF | 56% | C$_{11}$H$_{23}$N$_8$OP$_3$ | 376.28 | 170 | 39.55 | 32.37 | 39.04 41.5 |
| 2 | H | (CH$_2$)$_2$ | ACOEt-EI*1-1 | 59% | C$_{10}$H$_{21}$N$_8$OP$_3$ | 362.25 | 112 | 39.68 39.78 | 36.33 | 43.3 37.3 |
| 3 | H | (CH$_2$)$_3$ | THF | 67% | C$_{11}$H$_{23}$N$_8$OP$_3$ | 376.28 | 145 | 38.45 | 19.04 | 38.24 |
| 4 | cyclohexyl | (CH$_2$)$_3$ | IE | 47% | C$_{17}$H$_{33}$N$_8$OP$_3$ | 458.43 | 101 | 38.34 | 19.48 | 39.95 |
| 5 | benzyl | (CH$_2$)$_2$ | ACOEt-EI 1-1 | 41% | C$_{17}$H$_{27}$N$_8$OP$_3$ | 452.38 | 144 | 39.7 | 31.67 | 40.2 |
| 6 | benzyl | (CH$_2$)$_3$ | ACOEt-EI 1-1 | 50% | C$_{18}$H$_{29}$N$_8$OP$_3$ | 466.41 | 133 | 38.56 | 20.89 | 39.35 |
| 7 | phenethyl | (CH$_2$)$_2$ | ACOEt-EI 1-1 | 60% | C$_{18}$H$_{29}$N$_8$OP$_3$ | 466.41 | 124 | 39.5 | 31.48 | 40.35 |
| 8 | phenethyl | (CH$_2$)$_3$ | ACOEt-EI 1-1 | 35% | C$_{19}$H$_{31}$N$_8$OP$_3$ | 480.43 | 116 | 38.4 | 20.42 | 38.68 |
| 9 | H | (CH$_2$)$_4$ | ACOEt | 40% | C$_{12}$H$_{25}$N$_8$OP$_3$ | 390.31 | 129 | | | |

*IE = isopropyl ether

EXPERIMENTS

Various pharmacological and toxicological tests were carried out on the compounds which form the object of the present invention.

1. Pharmacological Activity a) In Vitro cytotoxicity

The cytotoxic activity in vitro was evaluated by the determination of the IC$_{50}$ (concentration for which 50% inhibition of cell growth is obtained) on mouse L1210 leukemic cells.

The IC$_{50}$ is evaluated by means of a cell counter.

| Compound | IC$_{50}$ (μM) |
| --- | --- |
| 1 | 9 |
| 2 | 8.7 |
| 3 | 2.3 |
| 4 | 9.9 |
| 5 | 5.8 |
| 6 | 5.8 |
| 7 | 7.8 |
| 8 | 6.5 | b) In vivo

The antitumoral activity in vivo was evaluated on the P 388 model in the mouse. This model corresponds to leukemic cells grafted i.p. on day D.

The drug is administered in repeated dosage on D1, D3, D5.

The index "T/C" corresponds to the survival (%) of the treated animals as compared with the control animals.

The "T/C" of the products of the invention ranges from 130 to >300.

2. Toxicity

The compounds of the invention are of moderate toxicity in the doses tested, in terms of the hematological parameters and the growth rate, i.e., weight increases as a function of time.

3. Therapeutic Applications

In view of their pharmacological properties, the compounds of the present invention can be used in animal including human therapy in the treatment of cancer pathology.

The pharmaceutical preparations containing these active principles can be formulated for administration orally, intravenously, or intraperitoneally.

It is also possible to combine them with other pharmaceutically-and therapeutically-acceptable active principles.

REPRESENTATIVE PHARMACEUTICAL FORMULATION

For the preparation of an injectable pharmaceutical formulation, about 10 mg to about 200 mg of a compound according to the present invention is dissolved in two (2) ml of an aqueous solution buffered at a pH of about pH8 to about pH9, for example by the employment of a mixture of Na$_2$HPO$_4$.7H$_2$O and NaH$_2$PO$_4$.H$_2$O, the solution then being rendered isotonic by the addition of sodium chloride, generally in accord with conventional knowledge of the art.

Other pharmaceutical compositions or formulations of the active compounds of the invention may also be employed, and the foregoing is merely representative. All of the usual diluents, carriers, or adjuvants which are conventional in the art may be employed to facilitate administration of the compounds of the present invention, which obviously may be administered in combination with other active ingredients according to standard practice of the art. In any event, a pharmaceutical composition of the invention will contain an effective cytotoxic or antineoplastic amount of a compound of the invention in combination with a pharmaceutically-acceptable diluent or carrier. As indicated in the foregoing, the pharmaceutical composition may contain between about 10 and about 200 mg of active ingredient per unit dosage form.

The method of treatment according to the invention consists essentially of the step of administering to a living animal, including a human, suffering from a neoplastic disease or condition which is responsive to treatment with a compound of the invention and susceptible thereto, an effective antineoplastic amount of a compound of the present invention, preferably in the form of a pharmaceutical composition thereof in which it is present together with a pharmaceutically-acceptable carrier or diluent.

It will of course be apparent to one skilled in the art that the amount of the active ingredient must be an effective cytotoxic or antineoplastic amount and also that the neoplastic disease or condition treated must be one which is susceptible to treatment with a compound of the invention, that is, one which is responsive to treatment therewith. It will further be apparent at one skilled in the art that the exact form of the pharmaceutically-acceptable diluent, carrier, or adjuvant employed, as well as the particular pharmaceutical form employed, whether tablet, capsule, suppository, or injectable solution, will be dependent upon the exact condition involved, as well as the condition of the patient involved, and as usual in accord with the preferences and directions of the physician or veterinarian in charge.

It is therefore seen from the foregoing that new compounds, pharmaceutical compositions thereof, a method of treating and ameliorating susceptible neoplastic diseases or conditions with such a compound or pharmaceutical composition of the invention, and a method of making the same, have all been provided, and that all of the objects of the invention have thus been fulfilled.

It is to be understood that the invention is not to be limited to the exact details of operation of exact compounds, compositions, methods, or procedures shown and described, as obvious modifications and equivalents will be apparent to one skilled in the art.

We claim:

1. A compound selected from those having the Formula I

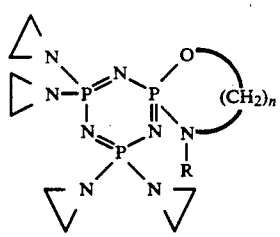

in which:

R represents hydrogen, linear, branched or cyclic C$_{1-6}$ alkyl, phenyl, or alkylphenyl phenyl (CH$_2$)$_m$—, m being 1 to 4 inclusive, and n=2, 3, or 4.

2. A compound according to claim 1, wherein R is selected from the group consisting of hydrogen, methyl, cyclohexyl, benzyl, and phenethyl.

3. A compound of claim 1 which is 4-methyl-7,7,9,9-tetra-1-aziridinyl-7,7,9,9-tetrahydro-1-oxa-4,6,8,10-tetraaza-5λ$^5$-7,9-triphosphaspiro-[4,5]-deca-5,7,9-triene.

4. A compound of claim 1 which is 11-phenylmethyl-2,2,4,4-tetra-1-aziridinyl-2,2,4,4,-tetrahydro-7-oxa-1,3,5,11-tetraaza-2,4,6λ$^5$-triphosphaspiro-[5,5]-undeca-1,3,5-triene.

5. A compound of claim 1 which is 2,2,4,4-tetra-1-aziridinyl-2,2,4,4-tetrahydro-7-oxa-1,3,5,12-tetraaza-2,4,6$\lambda^5$-triphosphaspiro-[5,6]-dodeca-1,3,5-triene.

6. A compound of claim 1 which is 7,7,9,9-tetra-1-aziridinyl-7,7,9,9-tetrahydro-1-oxa-4,6,8,10-tetraaza-5$\lambda^5$,7,9-triphosphaspiro-[4,5]-deca-5,7,9-triene.

7. A compound of claim 1 which is 2,2,4,4-tetra-1-aziridinyl-2,2,4,4-tetrahydro-7-oxa-1,3,5,11-tetraaza-2,4,6$\lambda^5$-triphosphaspiro-[5,5]-undeca-1,3,5-triene.

8. A compound of claim 1 which is 11-cyclohexyl-2,2,4,4-tetra-1-aziridinyl-2,2,4,4-tetrahydro-7-oxa-1,3,5,11-tetraaza-2,4,6$\lambda^5$-triphosphaspiro-[5,5]-undeca-1,3,5-triene.

9. A compound of claim 1 which is 4-phenylmethyl-7,7,9,9-tetra-1-aziridinyl-7,7,9,9-tetrahydro-1-oxa-4,6,8,10-tetraaza-5$\lambda^5$,7,9-triphosphaspiro-[4,5]-deca-5,7,9-triene.

10. A compound of claim 1 which is 4-(2-phenylethyl)-7,7,9,9-tetra-1-aziridinyl-7,7,9,9-tetrahydro-1-oxa-4,6,8,10-tetraaza-5$\lambda^5$,7,9-triphosphaspiro-[4,5]-deca-5,7,9-triene.

11. A compound of claim 1 which is 11-(2-phenylethyl)-2,2,4,4-tetra-1-aziridinyl-2,2,4,4-tetrahydro-7-oxa-1,3,5,11-tetraaza-2,4,6$\lambda^5$-triphosphaspiro-[5,5]-undeca-1,3,5-triene.

12. An antineoplastic pharmaceutical composition containing as active principle an effective antineoplastic amount of a compound of claim 1 together with a pharmaceutically-acceptable carrier or diluent.

13. The pharmaceutical composition of claim 12, wherein the compound is present in an amount of about 10 mg to about 200 mg per unit dose.

14. A method for the treatment of a neoplastic disease or condition, which is responsive to treatment with a compound of claim 1 and susceptible thereto, in a living being comprising the step of administering to the living being an effective antineoplastic amount of a compound of claim 1.

15. The method of claim 14 wherein the compound is administered in the form of a pharmaceutical composition thereof in which it is present together with a pharmaceutically-acceptable carrier or diluent.

* * * * *